US010596279B2

(12) United States Patent
Petrie

(10) Patent No.: US 10,596,279 B2
(45) Date of Patent: Mar. 24, 2020

(54) APPARATUS AND METHOD FOR STERILIZING BLOOD

(71) Applicant: Thomas R. Petrie, Sugar Hill, GA (US)

(72) Inventor: Thomas R. Petrie, Sugar Hill, GA (US)

(*) Notice: Subject to any disclaimer, the term of this patent is extended or adjusted under 35 U.S.C. 154(b) by 234 days.

(21) Appl. No.: 15/467,514

(22) Filed: Mar. 23, 2017

(65) Prior Publication Data

US 2017/0274105 A1 Sep. 28, 2017

Related U.S. Application Data

(60) Provisional application No. 62/312,739, filed on Mar. 24, 2016.

(51) Int. Cl.
A61L 2/00 (2006.01)
C12N 5/00 (2006.01)

(52) U.S. Cl.
CPC ........... A61L 2/0047 (2013.01); C12N 5/00 (2013.01); A61L 2202/11 (2013.01); A61L 2202/122 (2013.01); A61L 2202/14 (2013.01); A61L 2202/22 (2013.01)

(58) Field of Classification Search
CPC ................. A61L 2/0047; A61L 2202/22
See application file for complete search history.

(56) References Cited

U.S. PATENT DOCUMENTS

| 6,312,593 | B1 | 11/2001 | Petrie |
| 7,547,391 | B2 | 6/2009 | Petrie |
| 2004/0108198 | A1* | 6/2004 | Michishita ............ B01J 19/123 |
| | | | 204/157.67 |
| 2006/0157426 | A1 | 7/2006 | Petrie |
| 2007/0083144 | A1 | 4/2007 | Petrie |
| 2008/0102505 | A1 | 5/2008 | Petrie |
| 2009/0227931 | A1 | 9/2009 | Petrie |
| 2013/0317422 | A1* | 11/2013 | Levenson ............ A61M 39/16 |
| | | | 604/67 |
| 2014/0202962 | A1* | 7/2014 | Bilenko .................. C02F 1/325 |
| | | | 210/748.11 |

FOREIGN PATENT DOCUMENTS

| WO | 2006058062 A2 | 6/2006 |
| WO | 2006128047 A2 | 11/2006 |
| WO | 2008036285 A1 | 3/2008 |

* cited by examiner

Primary Examiner — Kevin Joyner

(57) ABSTRACT

A method and apparatus to neutralize or destroy pathogens in red blood cell concentrate (RBCC). The apparatus may include a lamp to provide ultra-violet (UV) light having a predetermined wavelength, a focusing member to focus the UV light from the lamp, a chamber assembly to receive the RBCC at a predetermined flow rate and to cause the received RBCC to be exposed to the focused UV light, and a controller. The chamber assembly may include a window and a bladder assembly. The bladder assembly may have a movable bladder portion. The controller may control movement of the bladder portion such that a space provided between the window and a surface of the bladder assembly, wherein the RBCC is caused to flow, enables the focused UV light to neutralize or destroy at least some of the pathogens in the RBCC during flow through the space.

4 Claims, 7 Drawing Sheets

APPARATUS AND METHOD FOR STERILIZING BLOOD

CROSS-REFERENCE TO RELATED APPLICATIONS

The present application claims the benefit of the filing date of U.S. Provisional Patent Application No. 62/312,739 filed Mar. 24, 2016 the disclosure of which is hereby incorporated herein by reference.

FIELD

The present disclosure relates to an apparatus and method to neutralize or destroy pathogens in red blood cell concentrate (RBCC).

BACKGROUND

Blood contains biological components critical to supporting life, which makes blood transfusions a life saver. Unfortunately, blood may also contain pathogens which may be harmful or undesirable to a patient. As a result, it is desirable to sterilize blood to remove these pathogens. However, critical biological components of the blood and pathogens may be similar in some respects and may both be affected by sterilizing agents or techniques. Accordingly, the challenge is to reduce the pathogen titer or concentration to an acceptable safe level with minimal or no damage to the critical biological components. Today, methods of blood sterilization may involve gamma ray, chemical additives and slow cooking. However, such methods may have a high cost and/or marginal reductions in the level of pathogens.

Two blood components which may be targeted for sterilization are plasma and red blood cells (RBC). Transfusions of plasma may replenish anticoagulants, minerals, needed proteins and blood volume lose.

While progress has been made in transfusion safety from infection, donor deferrals for at-risk behaviors, the introduction of more-sensitive viral-screening assays and the recent introduction of nucleic-acid amplification technology have nearly eliminated transmission of HIV and hepatitis C virus by blood transfusion in certain areas of the world. Nevertheless, risks of other infectious agents for which such robust screening tools have not been developed include blood borne pathogens that can be viral, bacterial or parasitic. As a result, such pathogens may be present in the global blood supply.

SUMMARY

Today, sterilization of plasma (or frozen plasma) may achieve a safe level. However, due to their shape, chemical and handling sensitivity, sterilization of red blood cells (RBC) remains a challenge. More specifically, red blood cells may be considered as having a dimpled donut shape, which can harbor infectious agents. In addition, red blood cells may be sensitive to processing chemicals, temperature and/or pressure. RBC transfusions may be used to reduce anemia (low hemoglobin), supply complimenting cellular minerals, post dialysis and blood loss.

Thus, the ability to provide sterile human whole blood and concentrated red cells (collection of red cells only "RBCC") has been a challenge. The present disclosure provides a technique which may neutralize pathogens in RBCC and avoid the inadvertent transmission of blood supply pathogens to patients.

Pharmaceutical companies are working hard to develop new approaches to combat drug resistance and the evolution of new infections. Many of today's drugs use altered, weaken or dead related bacteria and viruses to combat the infections. To research, identify and produce with precision is a difficult and challenging task.

The present technique and/or apparatus may deliver a precise and controlled level of UV irradiation containing wavelengths that can alter cellular, bacterial and viral biological properties at a controlled flow rate and controlled exposure and, as a result, is applicable for use in pharmaceutical antibiotic and vaccine development and process applications to inactivate bacteria and virus or alter their ability to function.

An aspect of the present disclosure is an apparatus to neutralize or destroy pathogens in red blood cell concentrate (RBCC). Such apparatus may include a lamp to provide ultra-violet (UV) light having a predetermined wavelength, a focusing member to focus the UV light from the lamp, a chamber assembly to receive the RBCC at a predetermined flow rate and to cause the received RBCC to be exposed to the focused UV light, and a controller. The chamber assembly may include a window and a bladder assembly, in which the bladder assembly may have a movable bladder portion. The controller may control movement of the bladder portion such that a space provided between the window and a surface of the bladder assembly, wherein the RBCC is caused to flow, enables the focused UV light to neutralize or destroy at least some of the pathogens in the RBCC during flow through the space.

Further, the space may have a thickness greater than 0 and less than or equal to 0.001 inches.

Furthermore, the predetermined wavelength may be 254 nanometers (nm), 265 nm, or 270 nm.

Additionally, the lamp may provide a maximum output energy value of 4.2 mw/cm$^2$±0.2 mw/cm$^2$ at the chamber window.

Still further, the focusing member may include a first slotted focusing portal which is fixedly arranged at a first distance from the chamber window. The first slotted focusing portal may have an opening with a length in a direction normal to a direction of the UV light from the lamp which corresponds to an arc length of the lamp.

Also, the focusing member may also include a second slotted focusing portal which is adjustably arranged so as to be movable between the lamp and the chamber window and have a second distance from the chamber window which is larger than the first distance. And, the second slotted focusing portal may have an opening with a length in the direction normal to the direction of the UV light from the lamp larger than the length of the opening of the first slotted focusing portal.

Another aspect of the present disclosure is a method for use with an apparatus to neutralize or destroy pathogens in red blood cell concentrate (RBCC). The method may include controlling movement of a movable bladder portion of a bladder assembly of the apparatus such that a space provided between a window and a surface of the bladder assembly, wherein the RBCC is caused to flow, enables focused ultra-violet (UV) light from a lamp of the apparatus to neutralize or destroy at least some of the pathogens in the RBCC during flow through the space. The UV light from the lamp may have a predetermined wavelength. And, the apparatus may include a focusing member to focus the UV light from the lamp, and a chamber assembly to receive the RBCC at a predetermined flow rate and to cause the received RBCC to be exposed to the focused UV light, in which the chamber assembly may include the window and the bladder assembly.

BRIEF DESCRIPTION OF THE DRAWINGS

A more complete appreciation of the present subject matter and the various advantages thereof can be realized by reference to the following detailed description in which reference is made to the accompanying drawings wherein like reference numbers or characters refer to similar elements.

DETAILED DESCRIPTION

Using the energy properties of ultraviolet (UV) light to sterilize whole blood or RBCC may be a safer alternative as compared to other techniques such as those involving chemicals. However, there may be a number of issues to satisfy or overcome in order to effectively use UV light.

One issue may be the penetration of UV light in blood in a depth direction. Such UV light depth penetration may be limited to only approximately 1-2 millimeters (mm).

Figure 1:
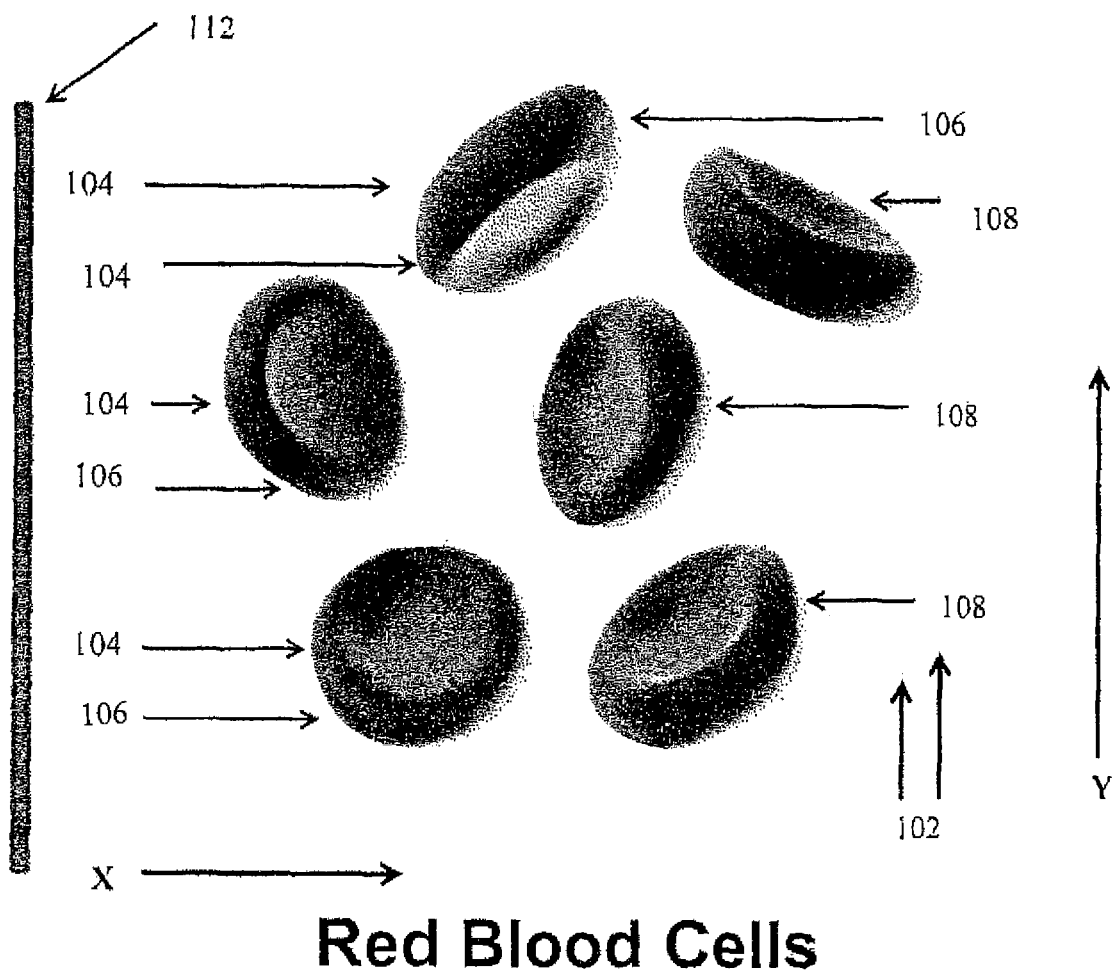
FIG. 1 is a diagram to which reference will be made in explaining an embodiment of the present disclosure.

Another issue may be due to the line-of sight output of UV light along with the shape of red cells and the concentration thereof which may cause UV light energy to not reach cells flowing behind other cells which are being exposed to UV light. For example and with reference to FIG. 1, consider a stream of red cells 102 flowing in a direction Y. In such situation, if UV light 104 outputted from a source 112 in a direction X is irradiated upon the stream of red cells 102, then only certain red cells 106 may actually be irradiated. As a result, other red cells 108 may not be irradiated by the UV light 104, as shown in FIG. 1.

Figure 2:
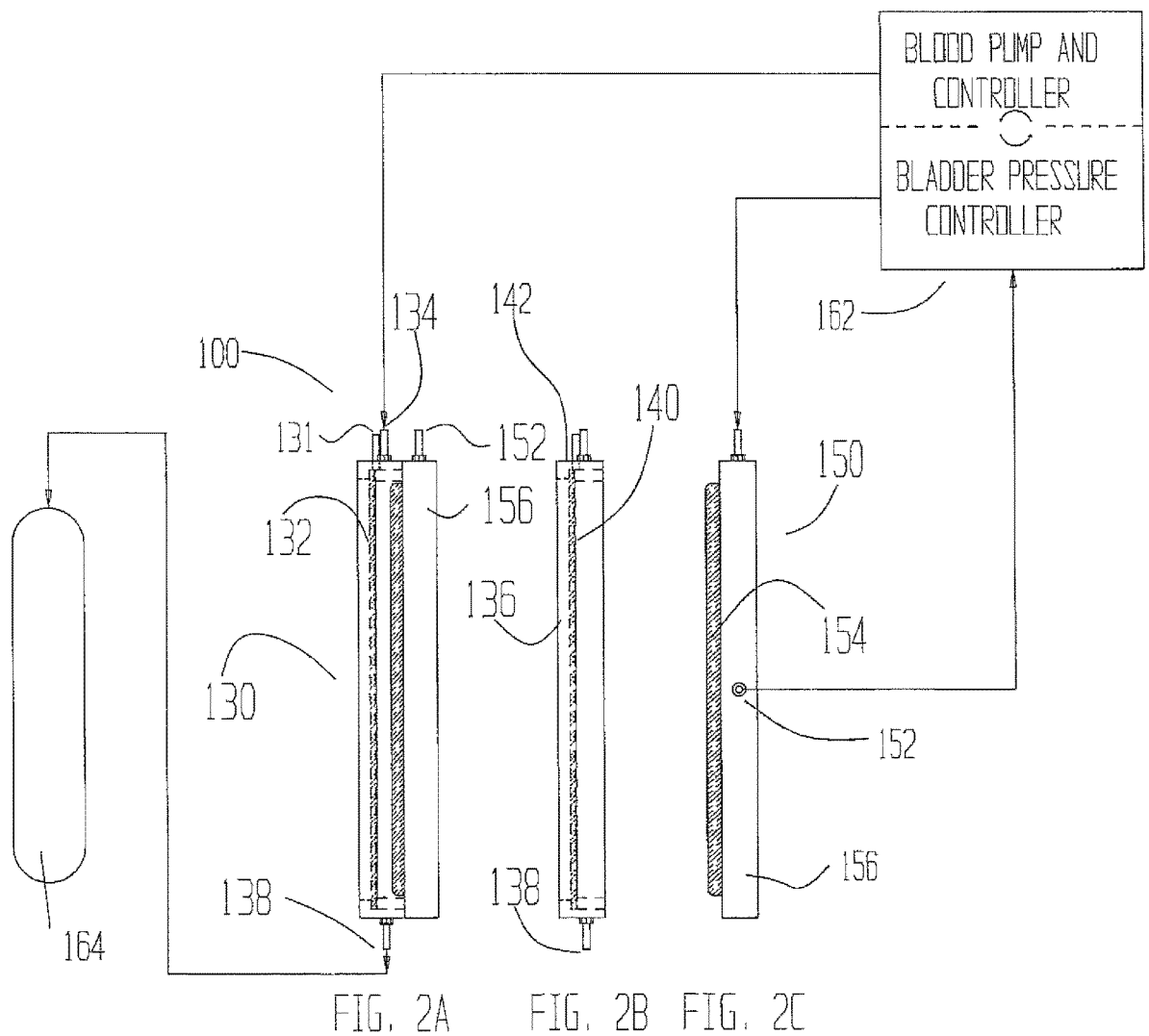
FIGS. 2A, 2B, 2C are views of an apparatus for sterilizing blood and blood components according to an embodiment of the present disclosure.

A sterilizing apparatus 100 illustrated in FIGS. 2A-C may enable whole blood or RBCC to be safely and effectively sterilized by use of ultraviolet (UV) light which may overcome the above-described issues. More specifically, the sterilizing apparatus 100 may provide a UV lamp sterilization process for whole blood or RBCC which may be non-pathogen specific and, as such, capable of inactivating most if not all pathogens.

The UV light effectiveness may be directly determined by exposure time and lamp energy and may be secondarily determined by temperature. The UV light energy exposure time may be controlled by a light chopper wheel 163 or an oscillating (opening/closing) window. (See FIGS. 4-6.)

The sterilizing assembly 100 may include a chamber portion 130 and a bladder assembly 150. See FIGS. 2A-C which illustrate different views of the sterilizing assembly 100.

The chamber portion 130 may include a chamber window 132, a chamber inlet port 134, a chamber main frame 136, a chamber outlet port 138, and a back reflector panel 140. The chamber portion 130 may overcome the above issues pertaining to limited UV penetration and light of sight by employing a number of novel techniques or design parameters including safely tumbling the blood cells so as to expose all blood cells to the UV light energy and prevent having untreated blood cells. Additionally, the bladder assembly 150 may also regulate the temperature using controlled air flow and/or liquid or electronic cooling systems.

The chamber window 132 may be a fused silica quartz window that allows the UV light energy to pass directly through to the cell's exposed surface. The chamber window 132 may have a length to enable the blood or blood component to be exposed multiple times to UV light energy during a sterilization operation. The length of the chamber window 132 may be dependent upon a number of factors including a length of a so-called effective portion of a UV lamp and a desired exposure time to UV light. In addition, the chamber window may have a width which is dependent upon a number of other factors which may include a diameter of the UV lamp and a distance or gap between the lamp and the window. As an example, when the UV lamp has a total length of approximately 4 inches with an effective portion length (will be described in further detail later) of approximately 2.5 inches and a diameter of approximately 1.0 inches and is located approximately 3.5 inches from the chamber window, the chamber window may have a length of approximately 2.5 to 3 inches and a width of approximately 1 inch. The chamber window 132 may be attached to the back reflector panel 140 to create a chamber 142 there between. The back reflector panel 140 should be smooth to predetermined criteria on the entire surface of the chamber window 132. Such predetermined criteria may be a mirror finish, or a surface texture having a 16 micron finish. The spacing between the chamber window 132 and the back reflector panel 140 may be set so as to determine the volume of the chamber 100.

The back reflector panel 140 may be configured to have adequate flexibility so as to completely or substantially completely lay flat against an interior surface of the silica quartz chamber window 132. Such back reflector panel 140 may be fabricated from rubber, plastic, fabric or metal. An interior surface of the back reflector panel 140 may have a highly reflective conductive coating thereon. An example of a material having such coating may be aluminized plastic.

The inlet and outlet ports 134/138 may be arranged so as to oppose each other, and may be configured to enable the blood or blood components to be supplied to or drained from the chamber 142. Further, such inlet and outlet ports may contain check valves to control the blood and/or blood component flow rates to predetermined values, such as from 0.5 to 5 milli-liters (ml) per minute. The chamber 142 may have a chamber vent 131 to alleviate back pressure and regulate chamber 142 internal atmospheric pressure during an inlet/outlet pulse.

The bladder assembly 150 may include inlet/outlet ports 152, a bladder 154, and a main frame portion 156. The bladder 154 may have a balloon type bladder configuration and/or a combination of a sealed bladder along with the main frame portion 156. The bladder 154 may be arranged to contact the back reflector panel 140 and configured to expand and contract in a pulsing manner so as to press the back reflector panel 140 against the interior of the chamber window 132 for a predetermined amount of time and then release therefrom. Such predetermined amount of time may be synchronized with a desired exposure time of the UV light to the sample (blood or blood components). As an example, UV irradiation level or power may have a value of approximately 0.1 mw (milli-watts) to 20 mw per square centimeter and may be applied to the blood or blood component sample for a one second exposure. Alternatively, the back reflector 140 may be an integral part of the bladder assembly 150.

The bladder 154 may be expanded and relaxed by any one of a number of techniques such as by using air pressure and air vacuum, by using circulating fluids, or by using mechanical means (e.g., arm or screw driven disc, roller or a series of rollers).

The bladder assembly 150 may be an integral part of or separate from the chamber assembly 100. The bladder assembly 150 may use one, two or three inlet and outlet ports to control the expansion and relaxation of the bladder 154.

The bladder assembly 150 expansion and relaxation timing sequence may be controlled and synchronized with a series of sensors and an electronic pumping/circulating system or electronic control mechanical system 162. The bladder 154 may be made from rubber, plastic, fabric, metal or a combination of materials.

The bladder assembly 150 design may maintain a fixed internal bladder pressure, which may eliminate or minimize the timing association to the chamber flow rate.

The fixed pressure bladder 154 may expand, increasing pressure on the initial chamber 142 inlet flow pulse and during the chamber inlet flow dwell the bladder 154 maintains pressure and forces the blood or blood components against the internal side of the chamber window 132.

Figure 3:
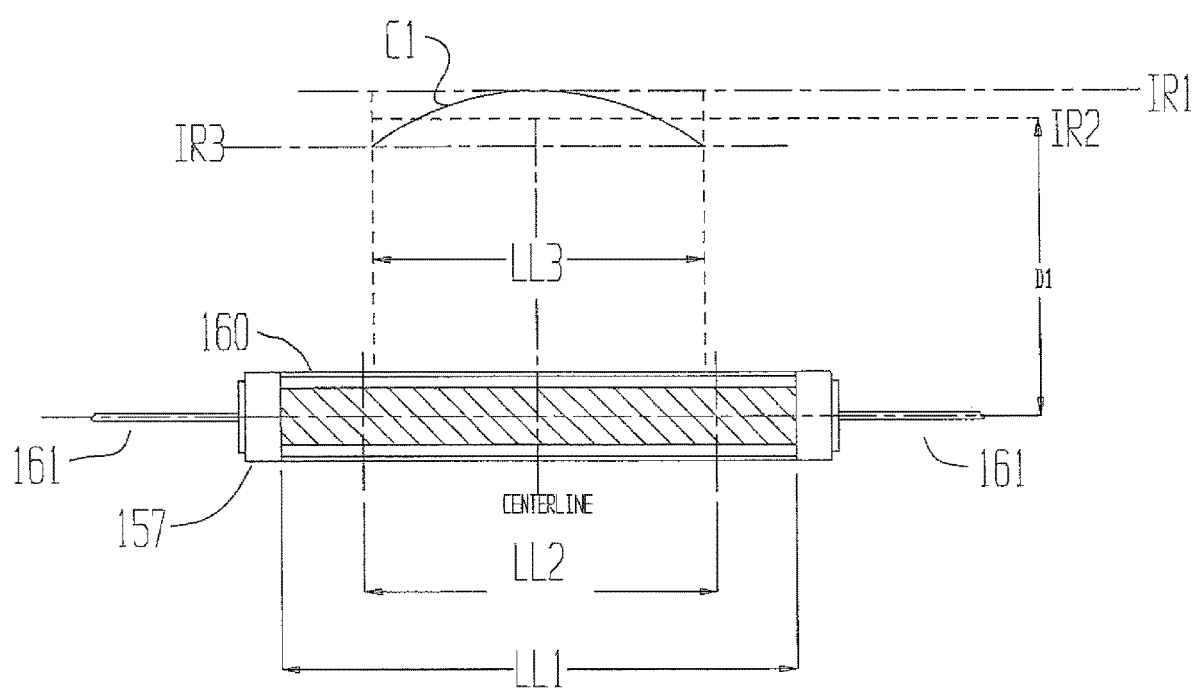
FIG. 3 is a diagram of a lamp according to an embodiment of the present disclosure.

Next, and with reference to FIG. 3, lamp 157 will be described.

The lamp 157 may be a medium pressure mercury type lamp and may have a length LL1 of approximately 3 inches, which may include a fused silica quartz crystal jacket 160 and special anodes 161. (See FIGS. 3 and 5.) The anode leads 161 connected to the lamp 157 regulate quality power source. The anodes 161 may enable multiple strikes to be performed daily without ignition failure. Additional gases and organics may be added internally to the lamp 157 to produce a stable predetermined wavelength output, such as 254 nanometers (nm), 265 nm, 270 nm. The fused silica quartz crystal jacket 160 isolates the lamp-on state from external temperature fluctuations and maintains the internal lamp-on temperature. At steady state, the temperature of the lamp 157 will maintain a stable lamp output energy and prevent premature loss of ignition.

The lamp 157 may have an arc length LL2 of approximately 2.5 inches, which is produced by the spacing of the anodes 161. The highest arc energy output of the lamp 157 is at the center of the lamp 157 and the arc energy output decreases from the center of the arc outward. A stable output portion of the lamp 157 (which may have a constant value output to within a predetermined variation - - - such as 10% variation) may exist in the center portion of the lamp 157 and may have a length LL3 of approximately 2 to 2.25 inches.

The maximum output energy value from the lamp 157 (IR1) may have a value of 4.2 mw/cm$^2$±0.2 mw/cm$^2$, at the chamber exposure window 132. Such energy value may be set by adjusting distance D1 between the lamp 157 and the chamber exposure window 132 of the chamber portion 130 of the sterilizing assembly 100. (See FIGS. 3-5.)

Figure 4:
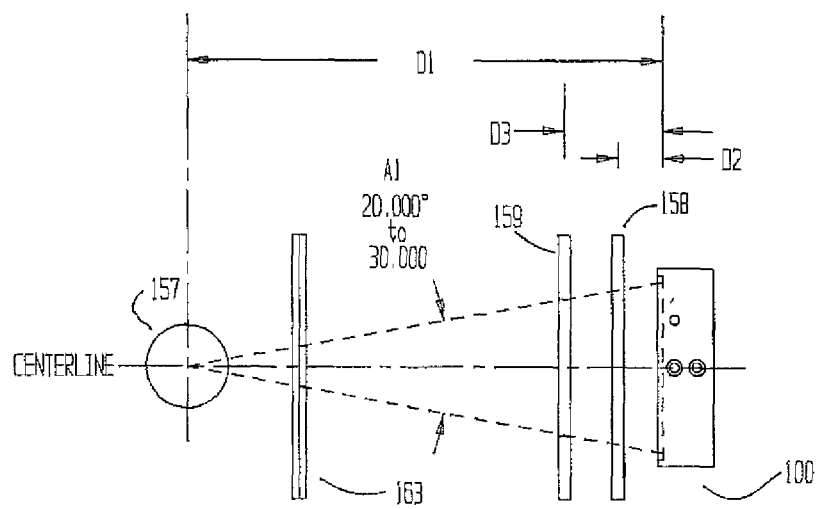
FIG. 4 is a top view of the lamp, fixed focusing portal, adjustable focusing portal, optional light chopper, and chamber according to an embodiment of the present disclosure.
Figure 5:
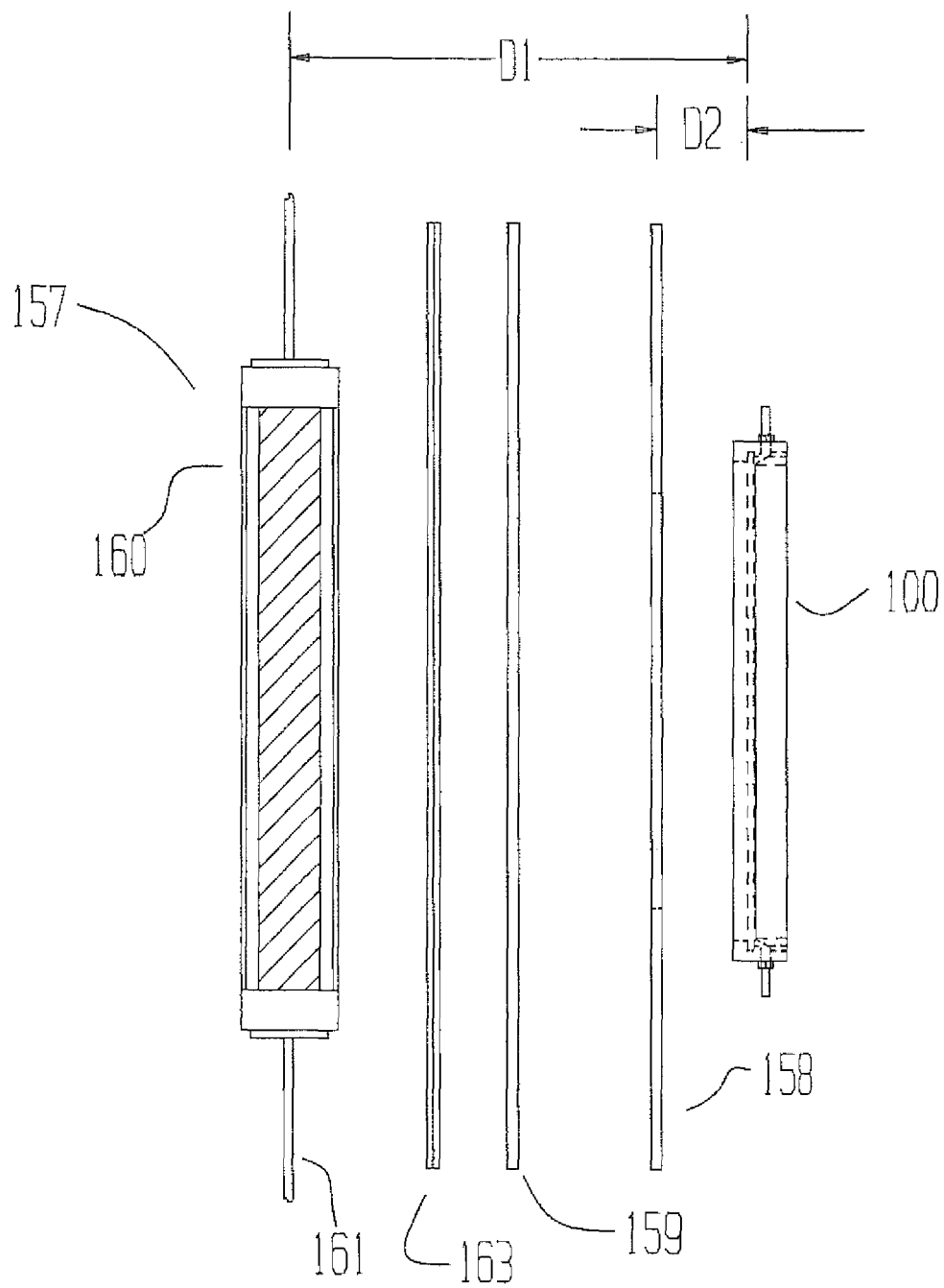
FIG. 5 is a front view of the lamp, fixed focusing portal, adjustable focusing portal, optional light chopper, and chamber according to an embodiment of the present disclosure.
Figure 6:
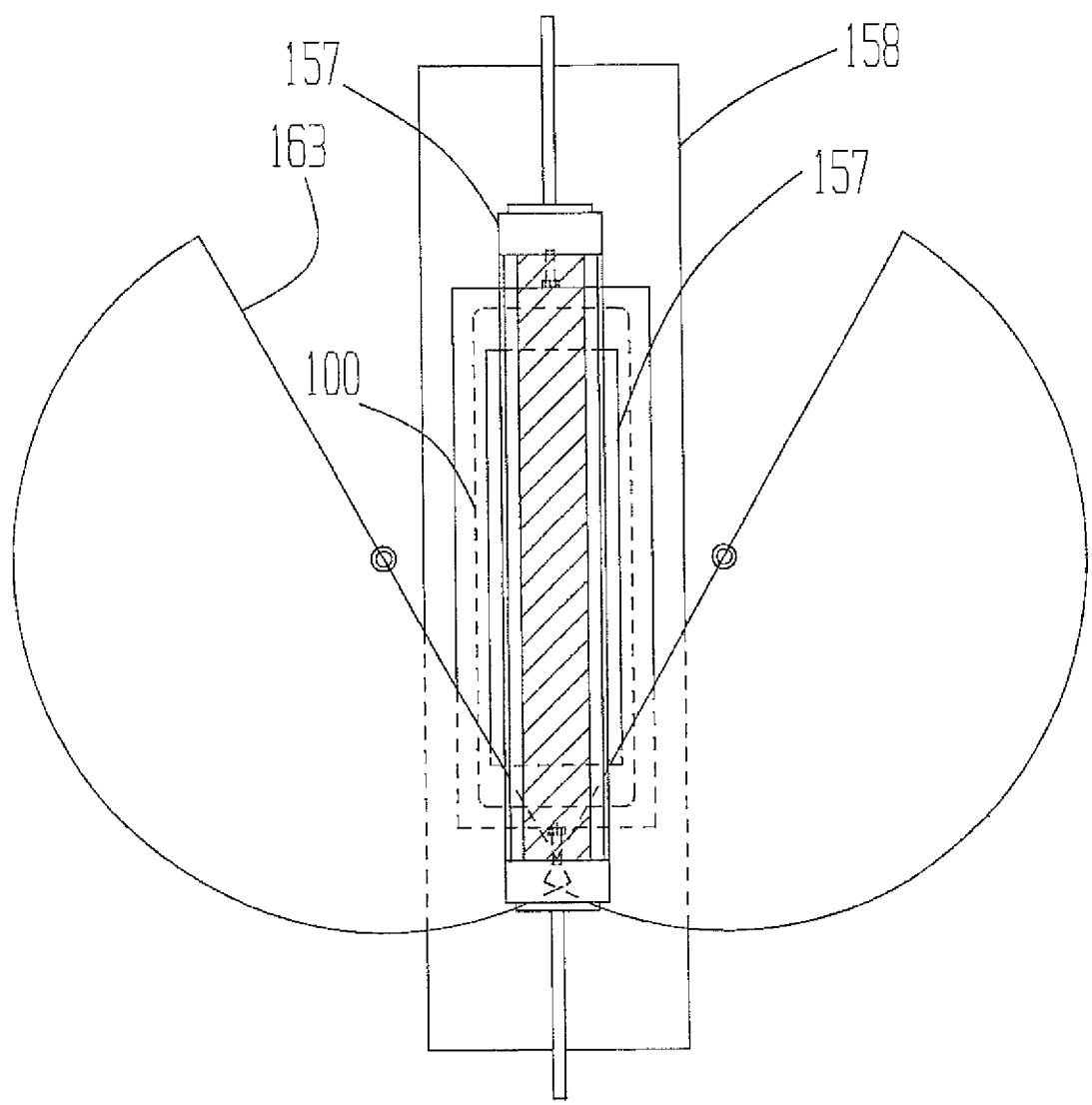
FIG. 6 is a side view of the lamp, fixed focusing portal, adjustable focusing portal, optional light chopper and chamber according to an embodiment of the present disclosure.

A fixed slotted focusing portal 158 has an opening with a length which may correspond to LL2 of the lamp 157. The fixed slotted focusing portal 158 may be arranged at a distance D2 from the chamber exposure window 132 of the chamber portion 130 of the sterilizing assembly 100 as shown in FIGS. 4-5. An adjustable slotted focusing portal 159 may have an opening with a length which may be larger than that of portal 158. The portal 159 may be movable between the lamp 157 and chamber exposure window 132 and may have a distance D3 from the chamber exposure window 132 of the chamber portion 130 of the sterilizing assembly 100 which may be larger than distance D2, as for example shown in FIG. 4. The adjustable slotted focusing portal 159 may be positioned to create an energy path C1 of the lamp 157 which may have a 10° to 15° curve or angle in relationship to an arc center of the lamp 157 or a total angle A of 20° to 30°, as for example shown in FIG. 4. C1 curve locates the optimal energy path range from lamp 157 arc output. Minimal energy IR3 may have a value of 3.6 mw/cm$^2$±0.2 mw/cm$^2$ at the chamber window 132. Midpoint energy IR2 may have a value of 3.9 mw/cm$^2$±0.2 mw/cm$^2$. Due to the interaction between the lamp 157, arc energy output and the adjustable focusing portal 159, their positions may be adjusted to achieve the required energy values at the chamber exposure window 132.

Controller 162 may include a central processing unit (CPU) and a memory to which a program may be provided or stored. Such program when executed may enable the controller to synchronize the blood pump flow rate to the chamber port 134 and the inflate-deflate rate timing of bladder 154. Further, the program may cause the blood to flow in a forward and reverse pulse type motion with a predetermined timing. Such timing may cause the forward motion to be greater than the reverse motion. Additionally, the controller 162 may control operation of the lamp 157. As an example thereof, the controller may monitor a temperature and energy output of the lamp 157 by monitoring a sensor or sensors arranged to provide indications of temperature and energy output.

The program may be provided on a computer readable storage medium such as a hard disk drive or a Read Only Memory (ROM). Alternatively, this program may be provided on a removable medium (such as a flexible disk, a Compact Disk Read Only Memory, a flash drive) which may be inserted into or used with controller 162.

The irradiated blood or blood components may exit the chamber outlet port 138 and be dispensed into collection bag 164. (See FIG. 2A.)

Additionally, the sterilizing apparatus 100 may be subjected to heat so as to have the chamber portion 130 at a predetermined temperature, such as near human body temperature (97-100 degrees F.). The heat may be provided by a heater device (not shown). And, such heat and temperature may be controlled by the controller 162.

In Operation

The chamber assembly 100 and electronic pumping/circulating system and/or electronic controller 162 may control all or a number of operating parameters. Such operating parameters may include one or more of the blood and/or blood component flow rate, the thickness of the blood and/or blood component flow, mixing and exposure time to the UV light energy, and/or temperature of the chamber. All of these operating parameters may be set at the factory. Alternatively, all of these operating parameters may be set by an operator by, for example, use of an input device (not shown) for use with the controller 162 which may enable the operator to input one or more desired parameters. As another alternative, one or more parameters may be set at the factory and one or more parameters may be set by the operator. As a modification to this latter alternative, all parameters may be originally set at the factory and presented to the operator as default settings and any one or more of these default settings may be changed by the operator. Such control may be similar to that of an intra-aorta cardiac assist balloon pump and balloon angioplasty.

Actual settings of one or more of the operating parameters may depend upon a type of pathogen or a number of strands of the pathogen or the DNA/RNA structure of the pathogen which is intended to be destroyed or neutralized. For example, the flow rate or exposure time to UV light may have different settings for different pathogens with different strands or DNA/RNA structures.

As is to be appreciated, proper settings for the operating parameters may be crucial to ensure that the desired pathogen or pathogens are destroyed or neutralized. Accordingly, care should be taken in this regard when operating the present apparatus.

During operation, the controller 162 may cause visual and/or audio indications of the operation to be provided for the operator. As an example, the controller 162 may provide indication signals indicative of the operation to a display device and/or a speaker (not shown), whereupon a visual representation and/or audio output may be provided to the operator. Such visual representation and/or audio output may provide the operator with real time status of the overall operation, actual measured values of one or more of the parameters (such as an actual temperature of the chamber, actual flow rate, and so forth), and/or a warning of any malfunction.

The blood and/or blood component flow rate or the combination of the pump/circulating output, bladder expansion/relaxation cycle and check values may be controlled by the pump/circulating system 162.

The blood and/or blood component flow may be exposed to the UV light energy once or multiple times.

The temperature of the chamber portion 130 may be controlled to be between 97-100 degrees F.

The exposure time may be controlled by a combination of a pump/circulating system 162, the chopper wheel 163 (FIGS. 4-6) and/an oscillating window (not shown).

An output from the controller 162 may be delivered to the chamber inlet port 134 causing the chamber assembly 100 to expand and displacing the back reflector panel 140 up against a surface of the bladder 154. The bladder 154 may be expanded whereupon the back reflector panel 140 may be moved toward the back surface of the chamber window 132 so as to create a space therebetween having a predetermined thickness (which may have a thickness value "T" in a range between greater than 0 and less than or equal to 0.001 inches - - - $0 < T \leq 0.001$ inches). Such thickness T may be along a direction normal to the back surface of the chamber window 132 and/or may be normal to the blood and/or blood component flow. As a result of this space, an ultra-thin film layer of blood or blood components may be created (which may also have a thickness value "T" in a range between greater than 0 and less than or equal to 0.001 inches $0 < T \leq 0.001$ inches). The ultra-thin film layer allows complete UV light energy penetration exposing the blood or blood components to direct and/or reflected UV light energy.

The bladder expansion and relaxation motion may produce multiple ultra-thin film layers as the blood or blood components flow through the chamber portion 130. This action may interrupt and release the flow keeping the cells in motion and orientating the cells to multiple exposures to the UV light. Additionally, due to the construction of the apparatus 100, the cells may be exposed to both direct exposure (which is directly from the lamp 157) and reflected energy/exposure from the back reflector panel 140. For example, the cells may be exposed to 2, 3, or 4 or more direct exposures, which may result in double exposures - - - that is, 4, 6 or 8 or more total exposures (i.e., both direct and reflected exposures). To insure proper effective use thereof, 3 or 4 direct exposures may be desirable.

For the present apparatus as described above, the flow rate of the blood or blood components through the chamber portion 130 may have a value of approximately 1 ml/second. Or, the present apparatus may subject the blood or blood components to a total time of exposure to UV light having one of the above mentioned wavelengths (i.e., 254 nm, 265 nm, or 270 nm) of approximately 5 seconds. Such exposure may be controlled by the chopper 163.

Figure 7:
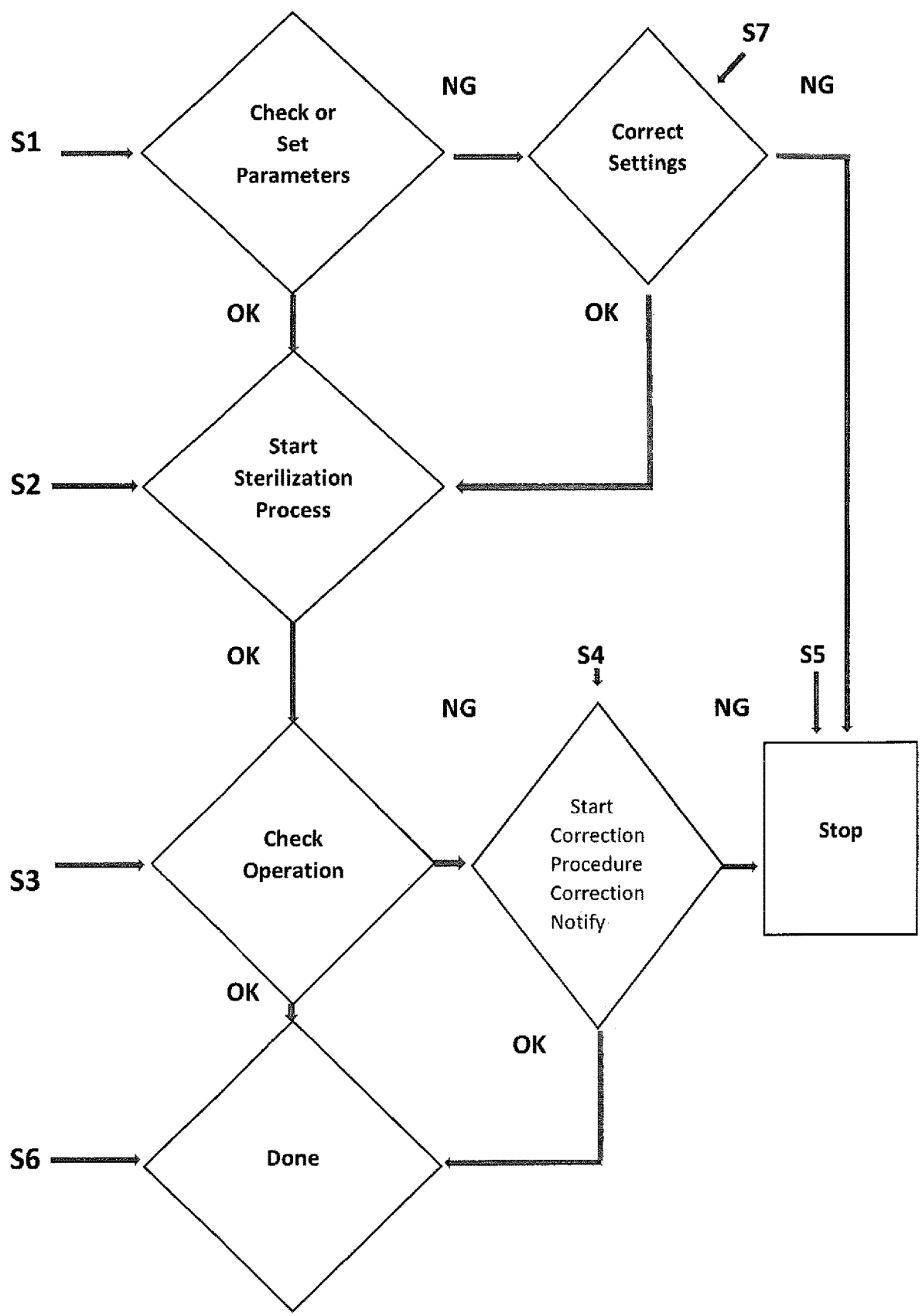
FIG. 7 is a flow chart of a procedure of the present apparatus.

FIG. 7 illustrates a method or procedure for use with the present apparatus. As shown therein, the parameters may be checked or set at Step S1. If all parameters are acceptable, then the method may proceed to Step S2 wherein the sterilization process may be started. Thereafter, the method may proceed to Step S3 wherein the operation may be checked or monitored. If the operation is determined to have been performed correctly, then the method may proceed to Step S6 wherein the method is completed. At such time, the blood or blood components which have been successfully subjected to the UV processing may be collected in the collection bag 164 (FIG. 2A).

On the other hand, if at Step S1 all of the parameters are not acceptable, then the method may proceed to Step S7 wherein incorrect settings may be corrected. If such corrections results in all acceptable parameters, then the method may proceed to Step S2. If, however, all incorrect settings are not corrected, then the method may proceed to Step S5 wherein the processing may be stopped.

If at Step S3 the operation is determined to have not been performed correctly, then the method may proceed to Step S4 wherein correction procedures may be started and/or a notification may be provided to the operator. If the correction procedures have successfully corrected the incorrect matter, then the method may proceed to Step S6. However, if the correction procedures have not successfully corrected the incorrect matter, then the method may proceed to Step S5.

The fused silica quartz chamber window 132 may acquire a negative surface charge in the presence of the blood or blood components (see White Paper by Behrens and Grier, et al, Grier Group Pub.) and influence the flow orientation of the cells and suspended pathogens. Alternatively, a surface charge may be applied to the back reflector panel 140 so as to influence the flow orientating of the cells and suspended pathogens.

Also, differences in surface tension of the chamber window 132 and back reflective panel 140 may be utilized to influence the flow characteristics of the cells and suspended pathogens.

Although the present disclosure has been described herein with reference to specific values of a number of parameters, the present apparatus and/or method may not be so limited. Alternatively, other values for any one or ones of these parameters may be used.

Further, although the present disclosure has been described herein as a technique which may neutralize or destroy pathogens in RBCC, the present apparatus and/or method may not be limited to use with only RBCC. As an example, such technique may be usable with RBC.

Although the apparatus and method herein has been described with reference to particular features and/or devices, it is to be understood that these are merely illustrative of the principles and/or applications of the present apparatus or method. It is therefore to be understood that numerous modifications may be made thereto and that other arrangements may be devised without departing from the spirit and scope of the present apparatus or method as defined by the appended claims.

The invention claimed is:

1. An apparatus to neutralize or destroy pathogens in red blood cell concentrate (RBCC), said apparatus comprising:
    A lamp to provide ultra-violet (UV) light having a predetermined wavelength;
    A focusing member to focus the UV light from the lamp;
    A chamber assembly to receive the RBCC at a predetermined flow rate and to cause the received RBCC to be exposed to the focused UV light; and
    A controller, in which the chamber assembly includes a window and a bladder assembly, said bladder assembly having a movable bladder portion; and
    In which the controller is programmed to control movement of the bladder portion at a predetermined set time such that a space provided between the window and a surface of the bladder assembly, wherein in the space the RBCC is caused to flow, enables the focused UV light to neutralize or destroy at least some of the pathogens in the RBCC during flow through the space.

2. The apparatus according to claim 1;
Wherein the focusing member includes a first slotted focusing portal which is fixedly arranged at a first distance from the chamber window, said first slotted focusing portal having an opening with a length in a direction normal to a direction of the UV light from the lamp which corresponds to an arc length of the lamp.

3. The apparatus according to claim 2;
Wherein the focusing member further includes a second slotted focusing portal which is adjustably arranged so as to be movable between the lamp and the chamber window and have a second distance from the chamber window which is larger than the first distance.

4. The apparatus according to claim 3;
Wherein said second slotted focusing portal has an opening with a length larger than the length of the opening of said first slotted focusing portal.

* * * * *